(12) United States Patent
Yadava et al.

(10) Patent No.: US 7,790,186 B2
(45) Date of Patent: Sep. 7, 2010

(54) PLASMODIUM VIVAX HYBRID CIRCUMSPOROZOITE PROTEIN AND VACCINE

(75) Inventors: Anjali Yadava, Rockville, MD (US); Christian F. Ockenhouse, Chevy Chase, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1193 days.

(21) Appl. No.: 11/334,161

(22) Filed: Jan. 18, 2006

(65) Prior Publication Data

US 2009/0196883 A1 Aug. 6, 2009

Related U.S. Application Data

(60) Provisional application No. 60/644,712, filed on Jan. 18, 2005.

(51) Int. Cl.
| | |
|---|---|
| *A61K 39/015* | (2006.01) |
| *A61K 39/002* | (2006.01) |
| *G01N 33/569* | (2006.01) |
| *C07K 14/445* | (2006.01) |
| *C12P 21/04* | (2006.01) |
| *C07H 21/04* | (2006.01) |

(52) U.S. Cl. ............... 424/268.1; 424/191.1; 424/192.1; 530/350; 530/387.9; 536/23.5; 536/23.7; 435/69.1; 435/69.7; 435/7.22; 435/320.1

(58) Field of Classification Search .................. None
See application file for complete search history.

(56) References Cited

U.S. PATENT DOCUMENTS 5,171,843 A 12/1992 Nussenzweig

FOREIGN PATENT DOCUMENTS

| EP | 0392820 | 10/1990 |
|---|---|---|
| WO | WO8807550 | 10/1988 |
| WO | WO9311157 | 6/1993 |
| WO | WO01/55181 | 8/2001 |

OTHER PUBLICATIONS

Barr, et al 1987; J. Exp. Med. 165:1160-1171.*
Yadava et al., 2007. A novel chimeric *Plasmodium vivax* circumsporozoite protein induces biologically functional antibodies that reccognize both VK210 and VK247 sporozoites. Infection and Immunity 75: 1177-1185.
Herrera et al., 2004. Use of long synthetic peptides to study the antigenicity and immunogenicity of the *Plasmodium vivax* circumsporozoite protein. International Journal of Parasitology 34: 1535-1546.
Rosenberg et al., 1989. Circumsporozoite protein heterogeneity in the human malaria parasite *Plasmodium vivax*. Science 245: 973-976.
Mann et al., 1994. Sequence variation in the circumsporozoite protein gene of *Plasmodium vivax* appears to be regionally biased. Molecular and Biochemical Parasitology 68: 45-52.
Udhayakumar V. et al., 1998. Immunogenicity of *Plasmodium falciparum* and *Plasmodium vivax* circumsporozoite protein repeat multiple antigen constructs (MAC). Vaccine 16: 982-988.
Herrera et al., 1997. Antigenicity and immunogenicity of multiple antigen peptides (MAP) containing *P. vivax* CS epitopes in *Aotus* monkeys. Parasite Immunology 19: 161-170.

* cited by examiner

*Primary Examiner*—Robert B Modesi
*Assistant Examiner*—Padma V Baskar
(74) *Attorney, Agent, or Firm*—Elizabeth Arwine

(57) ABSTRACT

Described in this application is a synthetic *P. vivax* circumsporozoite protein useful as a diagnostic reagent, for antibody production, and as a vaccine protective against infection with any strain of *P. vivax*.

19 Claims, 5 Drawing Sheets

Live IFA

Dry IFA

VK 247 (Type 2)

PLASMODIUM VIVAX HYBRID CIRCUMSPOROZOITE PROTEIN AND VACCINE

This application claims the benefit for priority under 35 U.S.C. Section 119(e) from Provisional Application No. 60/644,712 filed Jan. 18, 2005.

INTRODUCTION

*Plasmodium vivax* is the most abundant of all human malarias. In addition to being present in tropical and subtropical regions, the ability of the parasite to complete its mosquito cycle at temperatures as low as 15 degrees Celsius has also allowed it to be spread in temperate climates. It accounts for approximately 50% of all malaria cases worldwide. However, due to the fact that the disease caused by *P. vivax* is rarely lethal, the efforts to control *P. vivax* malaria (through vaccine development) are lagging far behind vaccine development against *P. falciparum*. Although *P. vivax* does not usually kill the patient, the sheer number of clinical cases, and the fact that it causes severe morbidity, contributes to serious economic impact in developing countries. In addition, there have been increasing numbers of reported cases of severe disease, resulting in anemia and death, caused by this parasite. A unique feature of *P. vivax* is that some 'strains' are capable of causing delayed infection by remaining latent in the liver before emerging into the peripheral circulation to manifest clinical symptoms. Thus, individuals that get infected in an endemic region may not present with symptoms for several months. When they return to areas that are not endemic for the disease, but do have the appropriate vector population, they can potentially cause the spread of disease in hitherto clean areas. Thus, it is necessary to focus efforts towards developing vaccines to control the global spread of *P. vivax* infections.

*P. vivax* malaria infection remains latent within the liver while the parasite is undergoing pre-erythrocytic shizogony. If the parasite is controlled at any stage before it escapes the liver there are no clinical symptoms of disease. Thus, the pre-erythrocytic stages of the malaria parasite are ideal targets for designing vaccines to prevent the symptomatic stage of the disease by killing parasites before they enter peripheral circulation.

The sporozoite has long been shown to induce protection in animal and human models against various malarias. Immunization with irradiated sporozoites leads to complete protection from a homologous challenge. However, using sporozoites to vaccinate large populations presents logistical problems.

The circumsporozoite (CS) protein present on the sporozoites of all plasmodia is the most abundant protein. It is involved in the motility and invasion of the sporozoite during its passage from the site of inoculation into circulation, from where it migrates to the liver and enters the hepatocyte (Mota, M M and Rodrigues, 2004, Cell Microbiol: 6, 1113-1118). As a consequence, the CS protein is a very appealing target for a vaccine. Studies in animal models and humans have shown promising results. The CS antigen has been shown to induce protection in rodent (Py and Pb) models and is a part of RTS,s, the most advanced malaria vaccine developed so far (Heppner et al. 2005, Vaccine 23, 2243-50) which is based on the CS protein of *P. falciparum*.

A recombinant *P. vivax* CS protein was expressed and tested as a vaccine in the early 80 s to 90 s with limited success (Collins et al., 1989, Am. J. Trop. Med. Hyg. 40, 455-64) and was not pursued further. Subsequently, due to the limitations of producing large amounts of pure protein, synthetic peptide-based vaccines have been developed. Recently, a Phase I study was carried out with the N-terminal, C-terminal and repeat region of PvCS and shown to induce antibody and IFN-gamma responses in vaccinated individuals (Herrera et al. 2005, Am. J. Trop. Med. Hyg. 73, 3-9). The vaccine was comprised of three long synthetic peptides corresponding to the N-terminal, Repeat region and C-terminal portions which ranged in size from 48 amino acids to 76 amino acids and were based on the sequence of the *P. vivax* Sal I parasite. The vaccine was based on linear peptides that represent three different parts of the CS molecule. They did not represent the CS protein in its entirety. Additionally these peptides did not take into account the variations found in the repeat region and were derived from a single strain of *P. vivax* (Sal-1) which is not representative of global *P. vivax* CS protein sequences. Other vaccines based on Multiple Antigen Peptides (MAP) were developed and tested in monkeys. MAPS are based on one or more epitopes that are cross-linked on a lysine backbone (Nardelli and Tam, 1995, Pharm. Biotechnol. 6, 803-19).

Synthetic vaccines present several drawbacks. Due to technical limitations in the length of synthetic peptides that can be made, these vaccines can not represent the entire protein, but only fragments of a protein. Additionally, these vaccines are limited in the sequences that are incorporated in them, and therefore would not recognize most global constructs. We therefore decided to explore the feasibility of a recombinant protein-based vaccine utilizing new advances in the field of biotechnology. Despite being studied for several years, the structure, and exact significance of the various parts of the CS molecule are not clearly known. There are several studies alluding to the significance of several regions of the CS molecule. CS sequence from all plasmodia show dramatic differences, with no general sequence conservation. There are, however, two motifs, a 5 amino acid sequence at the N-terminal immediately preceding the repeat region, known as Region I (KLKQP, SEQ ID NO:1), that shows complete sequence conservation in all the plasmodia sequenced so far. The second motif, located at the C-terminal end of the molecule, has strong sequence and motif conservation among all plasmodia. This region is known as Region II plus (CSVTCG, SEQ ID NO:2). Both Region I and Region II plus have been shown to be involved in binding to hepatocytes. Generating an immune response against these motifs could prevent a receptor-ligand interaction, a feature important in preventing the establishment of infection.

The bulk of the CS molecule of all Plasmodia is constituted by a central repeat region. The repeat regions vary for each *Plasmodium* species. The central repeat region of *P. falciparum* comprises of NANP/NVDP repeats. All sequenced strains of *P. falciparum* have a common and highly conserved repeat sequence. *P. vivax* has two distinct forms of the CS protein designated VK210, or Type 1, and VK247, or Type 2. These two forms are almost identical at the N and C terminal, but differ in the central repeat region. The repeat regions were initially identified when antibodies against what are now known as the VK210 parasite failed to recognize certain sporozoites. Thus, antibodies directed against the repeat region of the two types do not cross-react with each other. While a majority of the field infections are attributed to VK210 sporozoites, a significant number of VK247 infections are observed world-wide, either as single, or mixed (along with VK210) infections.

We designed a novel, 'immunologically optimal' synthetic construct that incorporates the major components of CS, but is different from the natural molecule. Specifically, our construct includes the N- and C-terminal parts of the CS protein, including Region I and Region II Plus, along with the amino acid repeat regions of both the VK210 and VK247 sequences. Traditionally, vaccines have been based on Sal 1 or Belem strains of P. vivax. These strains have VK210 (Type 1) repeats that have two major amino acid variations (GDRAAGQPA, SEQ ID NO:3, and GDRADGQPA, SEQ ID NO:4). Far-Eastern isolates, on the other hand, show more diversity in their repeats. Thus, using the Korean isolate, a VK210-like parasite, as a template, we have included variant CS repeat sequences encoded in all P. vivax strains that have been sequenced to-date (GDRAAGQPA, SEQ ID NO:3; GDRADGQPA, SEQ ID NO:4; GDRADGQAA, SEQ ID NO:5; GNGAGGQPA, SEQ ID NO:6; GDGAAGQPA, SEQ ID NO:7, GDRAARGQAA, SEQ ID NO:8, GNGAGGQAA, SEQ ID NO:9). In addition, our synthetic molecule includes a single copy of the major VK247 (Type 2) repeat (ANGAGNQPG, SEQ ID NO:10). Another feature of some of the Asian isolates is the presence of a 12 amino acid insert immediately following the repeat region (GGNAANKKAEDA, SEQ ID NO:11). We have also included this insert in our construct. We designed a synthetic gene incorporating all these features and optimized for E. coli codons.

We present results on the expression, process development and immunogenicity of this novel hybrid molecule. High level expression of protein with >95% purity and low endotoxin levels has been achieved. Mice and rabbits immunized with this recombinant protein elicit potent humoral and cellular immune responses to the protein. Fine-specificity analysis demonstrates that we have achieved our goal of eliciting an immune response against both Type 1 and Type 2 parasites and we also generated antibodies against the 12 amino acid insert. In addition, we were able to detect antibodies to the 'AGDR' epitope that has previously been shown to be the epitope recognized by a protective monoclonal antibody. We also detect the presence of IFN-gamma following in vitro re-stimulation of splenocytes.

SUMMARY OF THE INVENTION

The present invention provides isolated and purified P. vivax CS hybrid nucleic acid and protein and a method for proper expression and purification of the PvCS-hybrid. The CS hybrid nucleic acid was designed with modifications to the wild-type gene sequence found in GenBank accession no. AJ278611 with the purpose of optimizing immunogenicity of the hybrid protein by 1) removing sequences that may interfere with the generation of an optimal immune response following vaccination, 2) including additional sequences to produce a novel hybrid that can serve as a pan-reactive vaccine to the two distinct types of CS that exist in nature, and 3) optimizing expression in E. coli.

There are several studies alluding to the significance of several regions of the CS molecule. CS sequence from all plasmodia show dramatic differences, with no general sequence conservation. There are, however, two motifs, a 5 amino acid sequence at the N-terminal immediately preceding the repeat region, known as Region I that shows complete sequence conservation in all the plasmodia sequenced so far (SEQ ID NO:1). The second stretch, which is slightly larger, shows sequence and motif conservation among all plasmodia. This region is known as Region II plus (SEQ ID NO:2). Both Region I and Region II plus have been shown to be involved in binding to hepatocytes. Generating an immune response against these motifs could prevent a receptor-ligand interaction, a feature important in preventing the establishment of infection.

In addition, the terminal region of the CS protein of P. falciparum has been shown to be important in hepatocyte binding (Rathore et al., 2002, J. Biol. Chem. 277, 7092-8). Since CS protein from all Plasmodia have similar gene structure and share functional similarity, we extrapolated the information obtained from P. falciparum to P. vivax. Therefrom, the amino terminus of the P. vivax sequence was included in our vaccine construct.

The VK210 isolates from the Far-East (Korea, China) as well as those isolated from Somalia show the presence of a 12 amino acid insert at the end of the repeat region. The role of this region is not known. However, parasites from these regions have a high preponderance of delayed infections. While the presence of this 12 amino acid insert may not be causal, we believe that the inclusion of this sequence in a new vaccine construct would be advantageous.

The bulk of the CS molecule of all Plasmodia is constituted by a central repeat region. The repeat regions vary for each *Plasmodium* species. *P. vivax* has two distinct forms of the CS protein designated VK210, or Type 1, and VK247, or Type 2. These two forms are almost identical at the N and C terminal, but differ in the central repeat region. The repeat regions were initially identified when antibodies against what are now known as the VK210 parasite failed to recognize certain sporozoites. Thus, antibodies directed against the repeat region of the two types do not cross-react with each other. While a majority of the field infections are attributed to VK210 sporozoites, a significant number of VK247 infections are observed in the field, either as single, or mixed (along with VK210) infections.

The repeat region is highly immunogenic. Immunization with sporozoites, or with recombinant CS protein (of other plasmodia) results in the generation of a predominant anti-repeat antibody response. A strong correlation has been observed between protection and anti-repeat antibody titers in clinical studies with RTS,s (unpublished observations, WRAIR), a *P. falciparum* malaria vaccine based upon the CS antigen. However, in addition to an anti-repeat response, other parts of the molecule appear to be necessary for complete sterile protection that includes both antibody-mediated and cell-mediated immune mechanisms. Therefore, designing a molecule with decreased number of repeats may allow for an immune response that transcends the repeat region. We decided to reduce the number of CS repeats from 20 to 9 in order to maximize possibility of generating a balanced immunological response directed against the repeat region as well as the conserved N- and C-terminal regions. Thus, while the construct still has the repeat sequence, and should be able to generate an immune response to the repeat region, it will not be overwhelmed by an anti-repeat response.

In order to accommodate all the known isolates, we designed a chimeric molecule in which the VK210 repeats were followed by a VK247 repeat. Thus, our vaccine will be able to target all the field isolates.

Due to the almost complete identity at the N-, and C-terminal regions, we decided to make a vaccine based on the VK210 backbone, with the addition of a VK247 repeat. The presumption was that the immune response to the N- and C-terminal regions is common and the addition of VK247 repeat sequence will encompass a complete response to the two types of isolates.

Additionally the repeat region of the parasites from the Far-East also shows more amino acid permutations in the repeat region. The exact functional role of the repeat region is unknown. However, because antibodies directed against the repeat region can neutralize infective stage sporozoites, we have designed a synthetic non-naturally-occurring CS-based construct that would encompass all the variations of the VK210 repeats.

Based on the criteria described above, we designed a synthetic vaccine based on the CS protein of *P. vivax*. Our vaccine was based on the CS isolate from Korea including several representative variations of the VK210 prototype sequence (GDRADGQPA, SEQ ID NO:4). We added a prototype VK247 sequence (ANGAGNQPG, SEQ ID NO:10) at the end of the VK210 repeats. Our final construct had 9 VK210-type and one VK247-type repeat sequences, each repeat consisting of 9 amino acids. The vaccine construct has the 12 amino acid insert following the repeat region. In addition, the construct has the N- and C-terminal regions, excluding the signal and anchor sequences.

Therefore, a major aim of the present invention resides in the production of large amounts of immunogenic hybrid PvCS for diagnostic, prophylactic and therapeutic purposes.

Therefore, it is an object of the present invention to provide a nucleic acid encoding PvCS-hybrid protein containing sequences coding for the N-terminal portion of CS protein including Region I, both Type 1 and Type 2 repeats, a sequence coding for a 12 amino acid insert, and the C-terminal portion of the CS protein including Region II plus.

It is another object of the present invention to provide recombinant PvCS-hybrid protein encoded by the nucleic acid described above, for use in diagnostic assays and for production of antibodies.

It is another object of the present invention to provide compositions comprising purified recombinant PvCS-hybrid protein.

It is yet another object of the present invention to provide novel vector constructs for recombinantly expressing PvCS-hybrid, as well as host cells transformed with said vector.

It is also an object of the present invention to provide a method for producing and purifying recombinant PvCS-hybrid protein comprising:

growing a host cell containing a vector expressing PvCS-hybrid protein in a suitable culture medium, causing expression of said vector sequence as defined above under suitable conditions for production of soluble protein and, lysing said transformed host cells and recovering said PvCS-hybrid protein such that it retains its native folding and is essentially free of host toxins.

It is also an object of the present invention to provide diagnostic and immunogenic uses of the recombinant PvCS-hybrid protein of the present invention, as well as to provide kits for diagnostic use for example in malaria screening and confirmatory antibody tests.

It is also an object of the present invention to provide monoclonal or polyclonal antibodies, more particularly human monoclonal antibodies or mouse monoclonal antibodies which are humanized, which react specifically with PvCS-hybrid epitopes, either comprised in peptides or conformational epitopes comprised in recombinant proteins.

It is also an object of the present invention to provide possible uses of anti-PvCS-hybrid monoclonal antibodies for malaria antigen detection or for therapy of chronic malaria infection.

It is yet another object of the present invention to provide a malaria vaccine comprising PvCS-hybrid protein of the present invention, in an amount effective to elicit an immune response in an animal against *P. vivax*; and a pharmaceutically acceptable diluent, carrier, or excipient.

It is another object of the present invention to provide a malaria DNA vaccine comprising a PvCS-hybrid DNA. It is another object of the present invention to provide a method for eliciting in a subject an immune response against any strain of *P. vivax* malaria, the method comprising administering to a subject a DNA fragment comprising a PvCS-hybrid DNA.

It is another object of the present invention to provide a method for eliciting in a subject an immune response against any *P. vivax* malaria, the method comprising administering to a subject a composition comprising PvCS-hybrid of the present invention.

It is another object of the present invention to provide a method for preventing malaria infection in an animal comprising administering to the animal the PvCS-hybrid of the present invention.

The vaccine according to the present invention is inherently safe, is not painful to administer, and should not result in adverse side effects to the vaccinated individual.

The present invention also provides vectors for the production of a recombinant PvCS-hybrid, host cells containing the vectors, a method for fermenting and inducing the host cells, and a method for isolating and purifying the recombinant protein.

All the objects of the present invention are considered to have been met by the embodiments as set out below.

DETAILED DESCRIPTION

Figure 1:
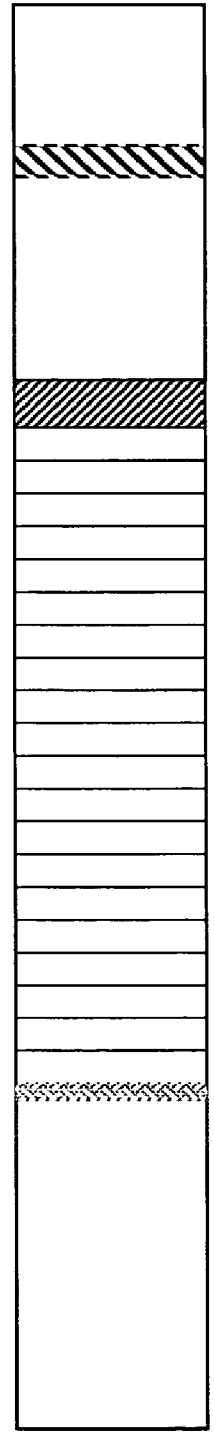
FIG. 1 depicts the structure of the chimeric CS molecule.

In the description that follows, a number of terms used in recombinant DNA, parasitology and immunology are extensively utilized. In order to provide a clearer and consistent understanding of the specification and claims, including the scope to be given such terms, the following definitions are provided.

In general, an 'epitope', is defined as a linear array of 3-10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primary structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, 'epitope' or 'antigenic determinant' means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, subtype (=genotype), or type (group)-specific variants, e.g. of the currently known sequences or strains belonging to *Plasmodium vivax* such as Sal I, Belem, Chesson, Vietnam, North Korean, or any other known or newly defined *Plasmodium vivax* strains or field isolates.

The term 'solid phase' intends a solid body to which the individual *P. vivax* antigen is bound covalently or by noncovalent means such as hydrophobic, ionic, or van der Waals association.

The term 'biological sample' intends a fluid or tissue of a mammalian individual (e.g. an anthropoid, a human), reptilian, avian, or any other zoo or farm animal that commonly contains antibodies produced by the individual, more particularly antibodies against malaria. The fluid or tissue may also contain *P. vivax* antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological fluid' refers to a fluid obtained from an organism. Some biological fluids are used as a source of other products, such as clotting factors (e.g. Factor VIII), serum albumin, growth hormone and the like.

The term 'immunologically reactive' means that the antigen in question will react specifically with anti-CS antibodies present in a body component from a malaria infected individual.

The term 'immune complex' intends the combination formed when an antibody binds to an epitope on an antigen.

The term 'PvCS-hybrid' as used herein refers to a chimeric molecule which includes the N- and C-terminal regions of *P. vivax* CS with Region I and Region II plus, respectively, also including several representative variations of the VK210 (Type 1) repeat sequence (SEQ ID NOs 3-9) and one or more VK247 (Type 2) repeat sequence (SEQ ID NO:10), and a 12 amino acid insert (SEQ ID NO:11). The term 'PvCS-hybrid' as used herein also includes analogs and truncated forms that are immunologically cross-reactive with the PvCS-hybrid protein. It is understood, after reading the following description and examples that other proteins can be designed which would still be immunologically similar to PvCS protein, including proteins which have truncated forms of the N- or C-terminal regions, proteins with a different number of variations of Type I repeat, proteins with a different number of major Type 2 repeat, or possibly including the minor Type 2 repeat (ANGAGDQPG, SEQ ID NO:14).

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' PvCS-hybrid protein intends a *Plasmodium* protein composition that is at least 35% pure.

The term 'essentially purified proteins' refers to proteins purified such that they can be used for in vitro diagnostic methods and as a prophylactic compound. These proteins are substantially free from cellular proteins, vector-derived proteins or other *Plasmodium* components. The proteins of the present invention are purified to homogeneity, at least 80% pure, preferably, 90%, more preferably 95%, more preferably 97%, more preferably 98%, more preferably 99%, even more preferably 99.5%.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces. Schizosaccharomyces, Kluveromyces, Pichia* (e.g. *Pichia pastoris*), *Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against malaria, whether partial or complete. A vaccine may also be useful for treatment of an infected individual, in which case it is called a therapeutic vaccine.

The term 'therapeutic' refers to a composition capable of treating malaria infection.

The term 'effective amount' for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of PvCS-hybrid for prophylaxis of malaria disease are about 0.01 to 1000 ug/dose, more preferably about 0.1 to 100 ug/dose, most preferably about 10-50 ug/dose. Several doses may be needed per individual in order to achieve a sufficient immune response and subsequent protection against malaria.

More particularly, the present invention contemplates essentially purified PvCS-hybrid protein and a method for isolating or purifying recombinant PvCS-hybrid protein, characterized in that it is immunologically reactive to all strains of *P. vivax*.

The term 'PvCS-hybrid' protein refers to a polypeptide or an analogue thereof (e.g. mimotopes) comprising an amino acid sequence (and/or amino acid analogues) defining at least one PvCS-hybrid epitope. Typically, the sequences defining the epitope correspond to the amino acid sequence of PvCS-hybrid (either identically or via substitution of analogues of the native amino acid residue that do not destroy the epitope). The PvCS-hybrid protein is encoded by a nucleotide sequence identified in SEQ ID NO:12. It is understood that even though the nucleic acid sequence has been optimized for expression in *E. coli*, also included would be analogous nucleic acids coding for the PvCS-hybrid and optimized for expression in another organism.

The PvCS-hybrid protein is defined in SEQ ID NO:13 and is based on the CS isolate from Korea including several representative variations of the VK210 prototype sequence (GDRADGQPA, SEQ ID NO:4), a prototype VK247 sequence at the end of the VK210 repeats, and a 12 amino acid insert following the repeat region. The final protein contains 9 VK210 type and one VK247 type repeat of 9 amino acids per repeat. Preferably, all of the Type-1 and the major Type-2 repeats are represented in the molecule. Of The 9 Type 1 repeats, 2 of the most prevalent repeats are repeated twice in PvCS-hybrid protein, hence it is possible that a single copy representation of all the known repeat variants, i.e. 7 Type 1, may suffice to provide proper folding and immune reaction Two of the type 2 (to take into account the second minor variant of the Type 2 repeat) may be are represented in a hybrid CS protein. The structure of CS is not known however, enough repeats must be present for correct helical folding.

The PvCS-hybrid antigen used in the present invention is preferably a full-length protein, or a substantially full-length version, i.e. containing functional fragments thereof (e.g. fragments which are not missing sequence essential to the formation or retention of an epitope). Furthermore, the *P. vivax* antigen of the present invention can also include other sequences that do not block or prevent the formation of the conformational epitope of interest. The presence or absence of a conformational epitope can be readily determined though screening the antigen of interest with an antibody as described in the Examples below (polyclonal serum or monoclonal to the conformational epitope) and comparing its reactivity to that of a denatured version of the antigen which retains only linear epitopes (if any).

The *P. vivax* antigen of the present invention can be made by any recombinant method that provides the epitope of interest. For example, recombinant expression in *E. coli* is a preferred method to provide non-glycosylated antigens in 'native' conformation. This is most desirable because natural *P. vivax* antigens are not glycosylated. Proteins secreted from mammalian cells may contain modifications including galactose or sialic acids which may be undesirable for certain diagnostic or vaccine applications. However, it may also be possible and sufficient for certain applications, as it is known for proteins, to express the antigen in other recombinant hosts such as baculovirus and yeast or higher eukaryotes The proteins according to the present invention may be secreted or expressed within compartments of the cell. Preferably, however, the proteins of the present invention are expressed within the cell and are released upon lysing the cells.

It is also understood that the isolates used in the examples section of the present invention were not intended to limit the scope of the invention and that an equivalent sequence from a *P. vivax* isolate other than Korea, i.e. from another strain, e.g. Chesson, Belem, Vietnam, Sal I, and other strains from different geographical locations and field isolates, can be used to produce a recombinant PvCS-hybrid protein using the methods described in the present application. Other new strains of *Plasmodium* may be a suitable source of PvCS-hybrid sequence for the practice of the present invention. Any new repeats could easily and readily be incorporated within the vaccine construct.

The PvCS-hybrid protein of the present invention is expressed as part of a recombinant vector. The present invention relates more particularly to the PvCS-hybrid nucleic acid sequence in recombinant nucleic acid AKI-ePVCS1-2. The PvCS-hybrid nucleic acid was cloned into a modified version of pQE60 vector from QIAGEN, Valencia, Calif. The vector was modified to introduce a Kanamycin resistance gene, and a lacI gene that constitutively expresses the lac repressor protein to enable tight regulation of foreign protein expression. The modified vector, pQE60-AKAI, or AKI for short, contained the ColE1 origin of replication and expresses the protein under the T5 promoter system. It is selectable under either Amplcillin or Kanamycin or under dual pressure. Other plasmids may be used such as pET vectors from Novagen and other commercial vectors that are compatible for making vaccines for human use The present invention also contemplates host cells transformed with a recombinant vector as defined above. In a preferred embodiment, *E. coli* strain BL21 that are lon and ompT protease deficient thereby reducing the proteolysis on recombinant protein. Other cells can be used as well, such as BLR. Other host cells such as insect cells can be used taking into account that other cells may result in lower levels of expression.

Eukaryotic hosts include lower and higher eukaryotic hosts as described in the definitions section. Lower eukaryotic hosts include yeast cells well known in the art. Higher eukaryotic hosts mainly include mammalian cell lines known in the art and include many immortalized cell lines available from the ATCC, including HeLa cells, Chinese hamster ovary (CHO) cells, Baby hamster kidney (BHK) cells, PK15, RK13 and a number of other cell lines. It is expected that when producing PvCS-hybrid in a eukaryotic expression system, extensive investigation into methods for expressing, isolating, purifying, and characterizing the protein would be required as eukaryotic cells post-translationally modify this protein and this would alter protein structure and immunogenicity.

Methods for introducing vectors into cells are known in the art. Please see e.g., Maniatis, Fitsch and Sambrook, *Molecular Cloning; A Laboratory* Manual (1982) or *DNA Cloning*, Volumes I and II (D. N. Glover ed. 1985) for general cloning methods. Host cells provided by this invention include *E. coli* containing pPvCS-hybrid.

A preferred method for isolating or purifying PvCS-hybrid as defined above is further characterized as comprising at least the following steps:

(i) growing a host cell as defined above transformed with a recombinant vector expressing PvCS-hybrid protein in a suitable culture medium, (ii) causing expression of said vector sequence as defined above under suitable conditions for production of a soluble protein, (iii) lysing said transformed host cells and recovering said PvCS-hybrid protein such that it retains its native conformation and is essentially pure.

Once the host has been transformed with the vector, the transformed cells are grown in culture in the presence of the desired antibiotic. For FDA regulatory purposes, it is preferable to use tetracycline or kanamycin. We use APS, Alternate Protein Source, medium to culture the cells. This medium does not contain any animal products. When cells reach optimal biomass density, in this case about 4-6, the cells are induced to produce the recombinant protein. The concentration of inducer, i.e. IPTG, added affects the maximal protein synthesis. It was found that a concentration of 0.1 mM IPTG was best however, a range of 0.05 to 0.5 mM would be sufficient to produce 80-100% of maximal. The cells are allowed to grow for an additional 2 hours after adding the inducer. The cells were then collected and lysed to release the recombinant protein. Preferably, lysis should occur at a paste to buffer ratio of 1:75 w/v to reduce viscosity and volume of sample loaded on Ni-NTA column. Preferably, lysis is in the presence of imidazole, about 50 mM, which reduces non specific binding of *E. coli* protein to Ni resin. Lysis is preferably at a temperature of about 0° C.-24° C., more preferably about 20° C. in order to retain native folding of the protein and to reduce proteolysis. A high salt concentration of about 0.5-1.0 M is preferable. Salts used include NaCl, NaP, or other monovalent ions in a pH range from about 6.2 to about 7.0 preferably, between about 6.2 to about 6.5

Preferably, the *E. coli* endotoxin is separated and removed from the recombinant protein. This can be done several ways. For PvCS-hybrid, endotoxin was removed by applying to a $Ni^{+2}$-NTA column. The removal of endotoxin depended on washing at low pH, about 5.8 to 6.5, preferably about pH 6.2, in high salt, about 0.5 to about 1.0 mM, preferably about 1 M NaCl, and 1% sarkosyl, at a flow rate of about 2.0-5.0 ml/min, preferably about 4 ml/min. The resin to cell paste ratio can be about 8 ml of matrix to 2 g of paste. The recombinant protein can be eluted by addition of high imidazole, about 400-600 mM, more preferably about 500 mM. in a phosphate buffer of about 10-30 mM, more preferably about 20 mM sodium phosphate buffer at a pH of 6.2.

The sample is diluted 4 times in 20 mM Phosphate buffer, pH 6.2 and further purified by ion exchange chromatography, preferably a Q-Sepharose FASTflow column (Amersham Pharmacia Biotech, Piscataway, N.J.) at about 1-5 ml of matrix to about 2 g of paste, more preferably, about 1.6 ml of matrix to about 2 g of paste. The sample is applied to the column and the flow-through is collected and applied to a second ion-exchange column, preferable, SP-sepharose FASTflow column (Amersham Pharmacia Biotech, Piscataway, N.J.) at about 1-5 ml of matrix to about 2 g of paste, more preferably, about 1.6 ml of matrix to about 2 g of paste.

The column is washed with 20 mM NaP buffer, pH 6.2 and the protein is eluted with high salt, preferably 300 mM in 20 mM NaP buffer, pH 6.2.

The present invention further relates to a composition comprising PvCS-hybrid for use as a vaccine and for in vitro detection of malaria antibodies present in a biological sample.

For in vitro detection of malaria antibodies present in a biological sample, the assay may comprise at least (i) contacting said biological sample with a composition comprising any of the PvCS-hybrid proteins or peptides derived from said protein which are immunologically identifiable with PvCS-hybrid, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, and (iv) detecting the presence of said immune complexes visually or mechanically (e.g. by means of densitometry, fluorimetry, colorimetry).

The present invention also relates to a kit for determining the presence of malaria antibodies, in a biological sample, comprising:

at least one peptide or protein composition as defined above, possibly in combination with other polypeptides or peptides from *Plasmodium* or other types of malaria parasite, with said peptides or proteins being preferentially immobilized on a solid support, more preferably on different microwells of the same ELISA plate, and even more preferentially on one and the same membrane strip, a buffer or components necessary for producing the buffer enabling binding reaction between these polypeptides or peptides and the antibodies against malaria present in the biological sample, means for detecting the immune complexes formed in the preceding binding reaction, and possibly also including an automated scanning and interpretation device for inferring the malaria parasite present in the sample from the observed binding pattern.

The immunoassay methods according to the present invention utilize PvCS-hybrid domains that maintain linear (in case of peptides) and conformational epitopes (proteins) recognized by antibodies in the sera from individuals infected with a malaria parasite. PvCS-hybrid antigens of the present invention may be employed in virtually any assay format that employs a known antigen to detect antibodies. A common feature of all of these assays is that the antigen is contacted with the body component suspected of containing malaria antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™ 1 or Immunlon™ 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of malaria antibodies in the antibody-antigen complexes is directly monitored. This may be accomplished by determining whether labeled anti-xenogeneic (e.g. anti-human) antibodies which recognize an epitope on anti-malaria antibodies will bind due to complex formation. In a competitive format, the amount of malaria antibodies in the sample is deduced by monitoring the competitive effect on the binding of a known amount of labeled antibody (or other competing ligand) in the complex.

Complexes formed comprising anti-malaria antibody (or in the case of competitive assays, the amount of competing antibody) are detected by any of a number of known techniques, depending on the format. For example, unlabeled malaria antibodies in the complex may be detected using a conjugate of anti-xenogeneic Ig complexed with a label (e.g. an enzyme label).

In an immunoprecipitation or agglutination assay format the reaction between the malaria antigens and the antibody forms a network that precipitates from the solution or suspension and forms a visible layer or film of precipitate. If no anti-malaria antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The PvCS-hybrid proteins, peptides, or antigens of the present invention will typically be packaged in the form of a kit for use in these immunoassays. The kit will normally contain in separate containers the PvCS-hybrid antigen, control antibody formulations (positive and/or negative), labeled antibody when the assay format requires the same and signal generating reagents (e.g. enzyme substrate) if the label does not generate a signal directly. The PvCS-hybrid antigen may be already bound to a solid matrix or separate with reagents for binding it to the matrix. Instructions (e.g. written, tape, CD-ROM, etc.) for carrying out the assay usually will be included in the kit.

Immunoassays that utilize the PvCS-hybrid antigen are useful in screening blood for the preparation of a supply from which potentially infective malaria parasite is lacking. The method for the preparation of the blood supply comprises the following steps: reacting a body component, preferably blood or a blood component, from the individual donating blood with PvCS-hybrid proteins of the present invention to allow an immunological reaction between malaria antibodies, if any, and the PvCS-hybrid antigen; and detecting whether anti-malaria antibody-PvCS-hybrid antigen complexes are formed as a result of the reacting. Blood contributed to the blood supply is from donors that do not exhibit antibodies to the native CS antigens.

The present invention further contemplates the use of PvCS-hybrid proteins, or parts thereof as defined above, for in vitro monitoring of the exposure to malaria infection resulting from *P. vivax* parasites or prognosing the response to treatment (for instance with chloroquine, mefloquine, Malarome) of patients suffering from malaria infection comprising:

incubating a biological sample from a patient with malaria infection with an PvCS-hybrid protein or a suitable part thereof under conditions allowing the formation of an immunological complex, removing unbound components, calculating the anti-PvCS-hybrid titers present in said sample (for example at the start of and/or during the course of therapy), and monitoring the natural course of malaria infection, or prognosing the response to treatment of said patient on the basis of the amount anti-PvCS-hybrid titers found in said sample at the start of treatment and/or during the course of treatment.

It is to be understood that smaller fragments of the above-mentioned peptides also fall within the scope of the present invention. Said smaller fragments can be easily prepared by chemical synthesis and can be tested for their ability to be used in an assay as detailed above.

The present invention also relates to a kit for monitoring malaria infection or prognosing the response to treatment (for instance to medication) of patients suffering from malaria infection comprising:

at least one PvCS-hybrid peptide as defined above, a buffer or components necessary for producing the buffer enabling the binding reaction between these proteins or peptides and the anti-PvCS-hybrid antibodies present in a biological sample, means for detecting the immune complexes formed in the preceding binding reaction, and possibly also an automated scanning and interpretation device for inferring a decrease of anti-PvCS-hybrid titers during the progression of treatment.

The present invention also relates to the use of a peptide or protein composition as defined above, for immobilization on a solid support and incorporation into a reversed phase hybridization assay, preferably for immobilization as parallel lines onto a solid support such as a membrane strip, for determining the presence or the genotype of malaria parasite according to a method as defined above. Combination with other type-specific or allele-specific antigens from other malaria parasites also lies within the scope of the present invention.

The present invention also relates to an PvCS-hybrid specific antibody raised upon immunizing an animal with a peptide or protein composition, with said antibody being specifically reactive with any of the polypeptides or peptides as defined above, and with said antibody being preferably a monoclonal antibody.

The present invention also relates to a PvCS-hybrid specific antibody screened from a variable chain library in plasmids or phages or from a population of human B-cells by means of a process known in the art, with said antibody being reactive with any of the polypeptides or peptides as defined above, and with said antibody being preferably a monoclonal antibody.

The PvCS-hybrid specific monoclonal antibodies of the invention can be produced by any hybridoma liable to be formed according to classical methods from splenic or lymph node cells of an animal, particularly from a mouse or rat, immunized against the *Plasmodium* polypeptides or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with malaria, or vaccinated against malaria. Such human monoclonal antibodies are prepared, for instance, by means of human peripheral blood lymphocytes (PBL) repopulation of severe combined immune deficiency (SCID) mice, or by means of transgenic mice in which human immunoglobulin genes have been used to replace the mouse genes.

The invention also relates to the use of the proteins or peptides of the invention, for the selection of recombinant antibodies by the process of repertoire cloning.

Antibodies directed to peptides or single or specific proteins derived from one or more certain strains may be used as a medicament, more particularly for incorporation into an immunoassay for the detection of *Plasmodium* strains for detecting the presence of PvCS antigens, or antigens containing PvCS-hybrid epitopes, for prognosing/monitoring of malaria disease, or as therapeutic agents.

Alternatively, the present invention also relates to the use of any of the above-specified PvCS-hybrid monoclonal antibodies for the preparation of an immunoassay kit for detecting the presence of PvCS-hybrid antigen or antigens containing PvCS-hybrid epitopes in a biological sample, for the preparation of a kit for prognosing/monitoring of malaria disease or for the preparation of a malaria medicament.

The present invention also relates to a method for in vitro diagnosis or detection of malaria antigen present in a biological sample, comprising at least (i) contacting said biological sample with any of the PvCS-hybrid specific monoclonal antibodies as defined above, preferably in an immobilized form under appropriate conditions which allow the formation of an immune complex, (ii) removing unbound components, (iii) incubating the immune complexes formed with heterologous antibodies, which specifically bind to the antibodies present in the sample to be analyzed, with said heterologous antibodies conjugated to a detectable label under appropriate conditions, and (iv) detecting the presence of said immune complexes visually or mechanically (e.g. by means of densitometry, fluorimetry, colorimetry).

The present invention also relates to a kit for in vitro diagnosis of a malaria antigen present in a biological sample, comprising:

at least one monoclonal antibody as defined above, with said antibody being preferentially immobilized on a solid substrate, a buffer or components necessary for producing the buffer enabling binding reaction between these antibodies and the malaria antigens present in the biological sample, and a means for detecting the immune complexes formed in the preceding binding reaction.

The kit can possibly also include an automated scanning and interpretation device for inferring the malaria antigens present in the sample from the observed binding pattern.

Monoclonal antibodies according to the present invention are suitable both as therapeutic and prophylactic agents for treating or preventing malaria infection in susceptible malaria-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting malaria infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before parasite can be controlled, and the induced immune response to the MAbs in the subject does not induce "serum sickness" in the subject. Preferably, the MAbs administered exhibit some secondary functions such as binding to Fc receptors of the subject.

Treatment of individuals having malaria infection may comprise the administration of a therapeutically effective amount of PvCS-hybrid antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to PvCS-hybrid, or an antibody capable of protecting against malaria in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

In a similar approach, another prophylactic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-PvCS-hybrid response (Linthicum, D. S, and Farid, N. R., Anti-Idiotypes, Receptors, and Molecular Mimicry (1988), pp 1-5 and 285-300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against malaria are intended to be provided to recipient subjects in an amount sufficient to effect a reduction in the malaria infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

In another aspect of the invention is provided a DNA vaccine against *P. vivax* malaria comprising a nucleic acid encoding PvCS-hybrid. DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

Therefore, the present invention relates to a DNA or cDNA segment which encodes *Plasmodium vivax* CS hybrid as described above. Genome sequences from different strains of *Plasmodium vivax* have been published and are publicly available. Other strains of *P. vivax* are expected to contain sequences at least 90% identical which will likely produce antigens capable of eliciting protective/neutralizing antibodies. Such strains include Belem, Chesson, Vietnam, North Korean, and others. It is envisioned that the PvCS-hybrid will provide cross protection against other *P. vivax* strains.

DNA or nucleic acid sequences to which the invention also relates include fragments of the PvCS-hybrid containing protective epitopes or antigenic determinants. Such epitopes may be linear or conformational as shown below in the Examples. The sequence of nucleic acids encoding antigens may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use. It is understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the CS genes of *P. vivax* are equivalents within the scope of the present invention.

The DNA encoding the desired antigen can be introduced into the cell in any suitable form including, the fragment alone, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques. Please see e.g., Maniatis et al., 1985 *Molecular Cloning: A Laboratory Manual* or *DNA Cloning*, Vol. I and II (D. N. Glover, ed., 1985) for general cloning methods.

The DNA, alone or in a vector, can be delivered by injection into the tissue of the recipient, oral or pulmonary delivery and inoculation by particle bombardment (i.e., gene gun) after coating a carrier particle with the DNA vaccine. Any of these methods can be used to deliver DNA as long as the DNA is expressed and the desired antigen is made in the cell.

Generally, the DNA vaccine administered may be in an amount of about 1-5 ug of DNA per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The present invention more particularly relates to a composition comprising at least one of the above-specified peptides or a recombinant PvCS-hybrid protein composition as defined above, for use as a vaccine for immunizing a mammal, preferably humans, against malaria, comprising administering a sufficient amount of the composition possibly accompanied by pharmaceutically acceptable adjuvant(s), to produce an immune response. The vaccine composition of the present invention is expected to provide cross-protection against infection from other *P. vivax* malaria strains.

Immunogenic compositions can be prepared according to methods known in the art. The present compositions comprise an immunogenic amount of a recombinant PvCS-hybrid proteins or peptides as defined above, usually combined with a pharmaceutically acceptable carrier, preferably further comprising an adjuvant.

The proteins of the present invention, preferably purified PvCS-hybrid derived from AKI-ePVCS1-2, are expected to provide a particularly useful vaccine antigen, since the antigen has been designed to contain all the known relevant parts that are important in host-parasite interactions. We have included parts of the molecule that are involved in Hepatocyte binding (N-terminal, Region I and Region II plus). We have included all the known repeats, both of the Type 1 and Type 2 parasites. In addition we have a 12 amino acid insert present in the strains associated with prolonged latency. In addition to several B cell epitopes we have also included T cell epitopes in our vaccine construct. Immunogenicity studies reveal that we are able to induce antibodies to the N-terminal, Repeat region and C-terminal parts of the molecule. These antibodies recognize the native parasite protein. They are able to agglutinate (and therby neutralize) live sporozoites. Additionally this protein is recognized by human sera from an endemic area of *P. vivax* transmission.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: montanide, aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The PvCS-hybrid protein of the invention may also be incorporated into Immune Stimulating Complexes together with saponins, for example QuilA (IS-COMS).

Immunogenic compositions used as vaccines comprise a 'sufficient amount' or 'an immunologically effective amount' of the proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, the strain of malaria infection, and other relevant factors. It is expected that the amount will fall in a relatively broad range that can be determined through routine trials. Usually, the amount will vary from 0.01 to 1000 ug/dose, more particularly from about 1.0 to 100 ug/dose most preferably from about 10 to 50 ug/dose.

The proteins may also serve as vaccine carriers to present other P. vivax antigens for inclusion into a multi-antigen subunit vaccine (e.g. other malaria antigens, such as DBP, PvTRAP, PvMSP2, PvMSP4, PvMSP5, PvMSP6, PvMSP7, PvMSP8, PvMSP9, and PvAMA1, RBP. In this use, the proteins of the invention provide an immunogenic carrier capable of stimulating an immune response to other antigens. The antigen may be conjugated either by conventional chemical methods, or may be cloned into the gene encoding PvCS-hybrid fused to the 5' end or the 3' end of the PvCS-hybrid gene. The vaccine may be administered in conjunction with other immunoregulatory agents.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the compounds, or vaccines, disclosed herein may be carried out by any suitable means, including parenteral injection (such as intraperitoneal, subcutaneous, or intramuscular injection).

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Materials and Methods

Design and Construction of Synthetic CS

Synthetic CS gene constructs were made based on the amino acids sequence of the Korean isolate of P. vivax. The construct started immediately following the signal sequence, with amino acids THCGH. The amino acid sequence for this construct was identical to the Korean isolate till Region I (KLKQP). Changes were made to the amino acid sequence in the repeat region. The wild-type Korean isolates have 20 repeats only two of which are identical to the classical GDRA [A/D]GQPA sequence. The remaining repeats are minor variants of this classical repeat. The synthetic construct was made to represent at least one copy of each of the repeats present in the wild-type isolates. [The two 'classical' repeats were represented twice.] In addition a single copy of the classical VK247 repeat, ANGAGNGPG, was included in the construct. This was followed by the C-terminal region. The construct did not have the anchor region, ending at ETDVCT (SEQ ID NO:13).

Codon usage frequencies for E. coli and P. vivax were calculated using the information available from the online database of Kazusa DNA Research Institute. A manual evaluation of the P. vivax CS gene sequence was performed and, when needed, P. vivax codons were modified for optimal expression in E. coli. The codon frequency of the selected E. coli codons was matched as closely as possible to the frequency of the P. vivax codon at each residue. Of the 257 amino acids encoding for the CS protein 167 (approximately 65%) of the codons were changed. The remaining 90 (35%) remained unchanged. The resulting synthetic gene differed from the native P. vivax gene at the nucleotide level while retaining exact amino acid identity to the wild-type sequence. The sequence of the harmonized gene is found in SEQ ID NO:12. All constructs were designed with appropriate restriction sites for cloning. Synthetic genes were constructed and assembled by BlueHeron Biotech Inc. (Bothell, Wash.) using GeneMaker, a proprietary gene synthesis platform. The synthetic genes were cloned into Blue Heron Bio pUC minus MCS vector, which lacks a multiple cloning site.

Cloning and Expression

Cloning of CS in expression vector: *E. coli* harboring the PUC vector containing the CS gene was grown and plasmid was isolated. The insert was released using appropriate restriction enzymes. The hybrid CS construct was cloned into the pQE60-AKI vector (Yadava & Ockenhouse 2003, Infect. Immun. 72, 4961-9) in frame with a 3' $His_6$ tag to enable purification. The resultant plasmid, designated AKI-ePvCS1-2, was used to transform *E. coli* XL1-blue (Stratagene, La Jolla, Calif.) cells and plasmid DNA was isolated from a positive clone to transform BL21(DE3) host cells for expression. Expression was confirmed using anti-$His_6$ antibodies (Clontech, Palo Alto, Calif.—CHECK) and monoclonal antibodies against both VK210 and VK247 isolates that were a kind gift from the Department of Entomology, WRAIR.

CS expression in *E. coli*: Since the protein is ultimately intended for human use, BL21(DE3) cells carrying the AKI-ePvCS1-2 plasmid were adapted to Alternate Protein Source (APS) medium that is free of animal protein. Clones were passaged five times on APS agar with Kanamycin. A single colony was used to make a glycerol stock which was used for subsequent experiments. After optimizing expression conditions at a small scale, clones were grown in APS broth with 0.8% glycerol, and 1% glucose and 25 ug/ml Kanamycin in a BioFlow3000 10 L fermentor (New Brunswick Scientific, Edison, N.J.). Cells were grown at 37° C. and induced at an $A_{600}$ between 4 and 6 with 0.1 mM IPTG. The cells were harvested 2 hours post-induction. The cell paste was frozen at −70° C. till processing.

Protein Purification

The *E. coli* cell paste was re-suspended in cracking buffer (1M NaCl, 50 mM Imidazole, 20 mM Sodium Phosphate, pH 6.2) and disrupted by microfluidization in a 110 s microfluidizer (Microfluidics Corp., Newton, Mass.). The sample was spun at 12000 rpm for 30 minutes. CS protein was purified from the soluble fraction. Briefly, the supernatant was incubated with 1% N-lauryl sarcosine (sarkosyl, Sigma, St. Louis, Mo.) for 30 minutes at room temperature and then loaded onto Ni-NTA superflow (Qiagen, Calif.) in the presence of 1% sarkosyl. The column was washed extensively with cracking buffer to remove all traces of sarkosyl. The cracking buffer was exchanged with cracking buffer without salt. The protein was eluted with 500 mM imidazole in 20 mM Sodium Phosphate, pH6.2. The sample was diluted to reduce the imidazole concentration to 125 mM and the passed over Q anion-exchange resin and the flow-through was passed over SP cation-exchange resin. Protein was eluted from the SP resin using 300 mM NaCl in 20 mM Sodium Phosphate, pH6.2. Sample was dialyzed into Phosphate buffered saline (PBS), pH 7.2 and protein concentration estimated using BCA (Pierce, Rockford, Ill.).

Antibodies

Mice: Outbred CD1 mice were primarily used for antibody studies. Inbred mice were used for analysis of genetic restriction of immune response to the protein. For this purpose, 8-12 week old female C57Bl/6 (H2-b), B10BR(H2-k) and Balb/c (H2-d) were obtained from Jackson laboratories (Bar Harbor, Me.). Mice were immunized with 10 ug protein in Complete Freund's adjuvant and boosted twice at three week intervals with 10 ug protein emulsified in incomplete Freund's adjuvant. In order to assess the effect of adjuvant on the immune response, and for cellular studies, mice were immunized with protein emulsified in Montanide ISA 51 and ISA 720 (Seppic, N.J.). Blood samples were collected 2 weeks following each immunization and sera were stored at −20° C. until use.

ELISA

Immulon 2HB plates (Dynatech, Alexandria, Va.) were coated overnight at 4° C. with 100 ul per well of recombinant CS protein, at a concentration of 1 ug/ml, diluted with PBS, pH 7.4. Plates were washed 4 times with PBS containing 0.1% tween 20 (PBS-T) to remove unbound antigen. The plates were blocked with PBS-Casein (Pierce, Rockford, Ill.) to prevent non-specific binding. Serum diluted in PBS-T was added for 2 hrs at room temperature. Horse-Radish Peroxidase labeled anti-mouse IgG (Promega, Madison, Wis.) was added to the plates, after washing, for an hour at room temperature. Reaction was developed with ABTS and read after 60 minutes at A405.

To assess the reactivity to the recombinant protein of humans following natural infection, sera from That symptomatic, smear positive patients from Mae Sod were tested in an ELISA. Sera were diluted 1:100 in PBS-T and incubated with recombinant CS coated, and blocked, plates for 2 hours at room temperature. The plates were washed and HRP-labeled anti-human IgG diluted 1:2000 was added for 1 hour at room temperature. Plates were developed with ABTS and read after 45 minutes at A405.

Heparan Sulfate Binding

Immunolon 4B plates were coated with 10 ug/ml of Heparan Sulfate (Sigma, Mo.) in water and the plates were allowed to dry overnight at 37° C. After washing with PBS-T, the plates were blocked with 1% BSA in PBS for an hour at room temperature. Recombinant CS protein starting at 5 ug/ml was serially diluted two-fold in PBS-T and allowed to bind to the heparan sulfate coated plate. The plate was washed and incubated with pooled sera from mice immunized with recombinant CS for an hour at room temperature. The plates were washed and incubated with HRP-labeled anti-mouse IgG diluted 1:2000 in PBS-T. Plates were developed with ABTS and read after 45 minutes at A405.

Western Blot

Recombinant CS protein was electrophoresed on 4-20% Bis-Tris SDS-polyacrylamide gels (Invitrogen, CA) and run under reducing, or non-reducing conditions using the MES buffer system. Samples were transferred electrophoretically onto nitrocellulose membranes (Invitrogen, CA). The membranes were blocked for up to 1 hour using nonfat milk in PBS containing 0.1% Tween 20 (PBS-T). After washing with PBS-T the blots were incubated for one hour at room temperature with primary antibody diluted in PBS-T. Alkaline phosphatase labeled anti-mouse (or anti-rabbit) IgG (Promega, WI/Kirkegaard and Perry, Gaithesburg, Md.) was added after washing off the primary antibody. The blots were developed with Nitro blue tetrazolium/5-bromo-4 chloroindol-3-yl phosphate solution (NBT/BCIP) (Promega, Madison, Wis.).

Immunofluorescence

Sporozoites obtained from mosquitoes infected with *P. vivax* (Pv210 and Pv247) were coated onto slides, air-dried and fixed with acetone. Slides were blocked with BSA diluted to 1% in PBS (PBS-BSA) for 30 min. Primary antibodies, diluted in PBS-BSA were added to the wells and the slides were incubated in a humidified chamber for one hour at room temperature. The slides were washed with PBS and FITC-labeled goat anti-mouse antibody (Promega, Madison, Wis.) was added for 30 min at room temperature. Slides were washed and mounted in fluoromount and viewed on an Olympus microscope.

For live IFA, Pv 210 sporozoites isolated from the salivary glands of infected mosquitoes were washed with PBS and then incubated with mouse anti-CS serum for 30 minutes. Anti-mouse Ig-FITC/TRITC (Kirkegaard and Perry, Gaithesburg, Md., DAKO labs) diluted 1:40 in PBS-0.1% BSA was added to the slide and after 30 minutes the slides were observed under the microscope. 40×, wavelength?

Example 1

Based on the criteria described above, we designed a synthetic vaccine based on the CS protein of *P. vivax*. Our vaccine was based on the CS isolate from Korea including several representative variations of the VK210 prototype sequence. We added a prototype VK247 sequence at the end of the VK210 repeats. Our final construct had 9 VK210 type and one VK247 repeat sequences, of 9 amino acid per repeat. The vaccine construct has the 12 amino acid insert following the repeat region. In addition, the construct has the N-terminal region including Region I, and the C-terminal region including Region II plus. Both the signal and anchor sequences were excluded.

FIG. 1 depicts the structure of the chimeric CS molecule.

Example 2

Expression and Purification of CS in *E. coli*

Figure 2A:
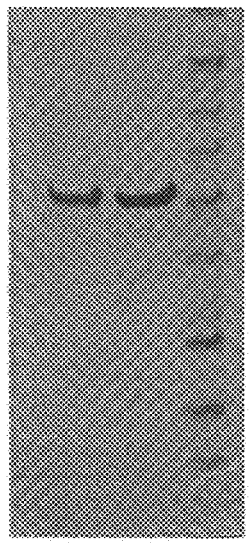
FIGS. 2A and 2B. Coomassie stained gel (2A) showing reduced and non-reduced recombinant ePV-CS immunoreactivity or recombinant ePV-CS1-2 to polyclonal antibodies against CS.
Figure 2B:
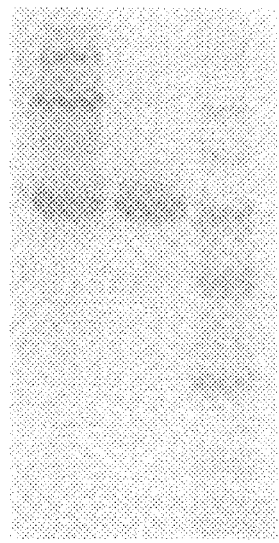

We optimized the codons for the CS gene and matched the frequency of the *P. vivax* CS codons to the *E. coli* codons. In all ~65% of the codons were altered and the remaining 35% were left unchanged. This codon optimized construct resulted in the expression of high levels of soluble protein (FIG. 2a) that was recognized by mAbs Pv210 and Pv247 that are specific for VK210 and VK247 sporozoites respectively (FIG. 2b). Recombinant VK210 CS that did not have a VK247 repeat was not recognized by mAb 247 (data not shown). The recombinant protein was purified to yield up to 1800 ug protein per 2 gram bacterial paste. The purification conditions were optimized to yield highly pure protein with very low endotoxin levels. We routinely purify protein that has endotoxin levels well below the range permissible range set for human vaccines.

Example 3

Heparan Sulfate Binding of Recombinant CS

Figure 3:
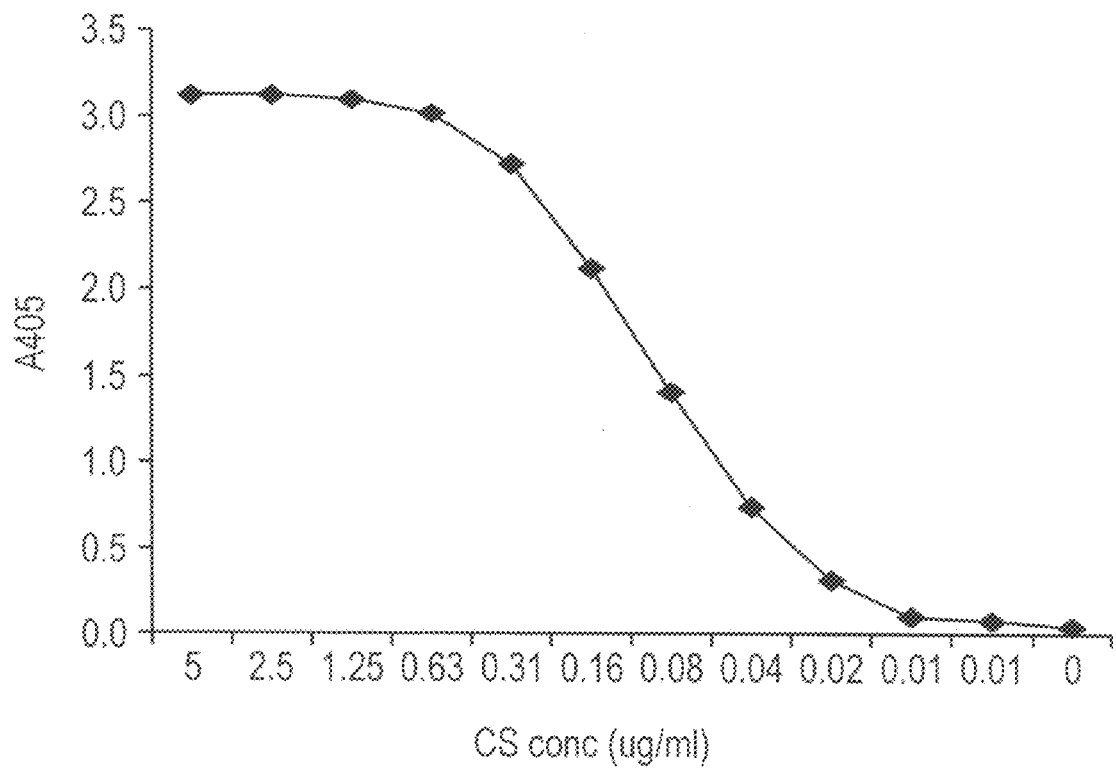
FIG. 3. Binding of recombinant ePV-CS to soluble Heparan sulfate.

Heparan sulfate present on hepatocyte serves as a receptor for the binding of sporozoites. CS molecule on sporozoites use heparan sulfate present on hepatocytes as a receptor for invasion. This binding is mediated by two charged motifs, Region I present on the N-terminal of the molecule, and Region II-plus present on the C-terminal of the molecule. In order to ascertain that modification (reduction) in the number of repeats has not affected the 'natural' conformation of the recombinant CS molecule such that the binding motifs are not exposed we tested the heparan sulfate binding of our molecule. Our results show that recombinant CS bound to soluble heparan sulfate in a dose dependent manner (FIG. 3) as well as to a HCO4, a hepatocyte cell line (data not shown). The binding to heparin sulfate was inhibited by soluble heparin sulfate.

Example 4

Immunogenicity of CS Protein in Mice

Figure 4:
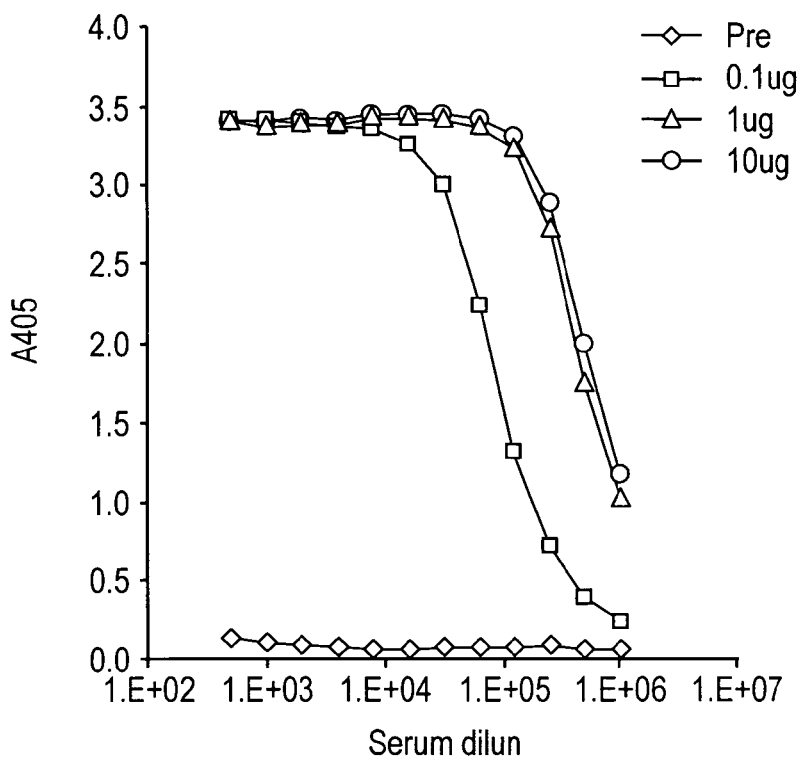
FIG. 4. Immunogenicity of CS: Immunization of CD1 mice with 10, 1, and 0.1 ug protein in Montanide 51.

Having confirmed its biological characteristics, we proceeded to the immunological characterization of the protein. In order to assess its immunogenicity, outbred CD1 mice were immunized with three different doses of the protein emulsified in Freund's adjuvant. We used outbred mice to simulate the variable haplotypes that a natural *plasmodium* infection encounters in the field. Mice were immunized with either 10 μg, 1 μg, or 0.1 μg protein. After the primary injection in complete Freund's adjuvant, mice generated antibodies as determined by ELISA (data not shown). After 2 boosts in Incomplete Freund's adjuvant, mice immunized with the lowest dose of 0.1 μg had titers of greater than 1×10$^6$, indicating that the protein is highly immunogenic (FIG. 4).

Figure 5:
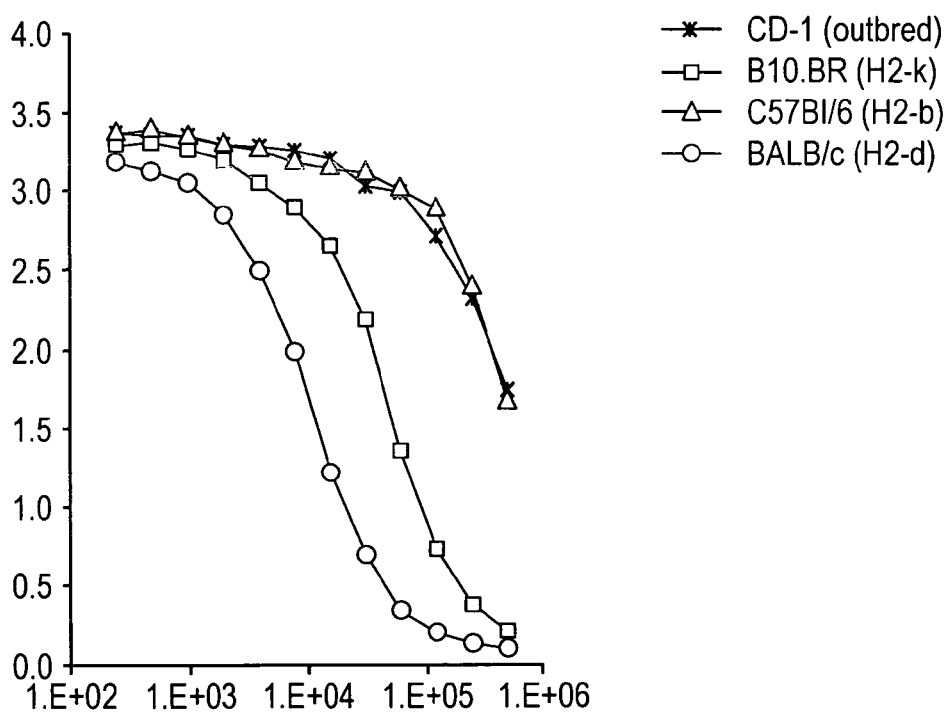
FIG. 5. Immunogenicity of CS: Immune response to CS (in Montanide 51) in 4 strains of mice.

CS is known to show genetic restriction in mice. We compared the immune responses of 4 different strains of mice. Outbred CD1 mice, three inbred strains, BALB/c, C57Bl/6 and B10.BR mice were immunized with 10 ug protein in Montanide 51. Results are shown in FIG. 5. Outbred CD1 mice and C57Bl/6, show very high titers (OD 1=840 and 757K respectively). The B10.BR mice which have a H2-K haplotype are intermediate responders with an OD 1 of ~100K. BALB/c mice have been shown to be poor responders to CS (good et al). In our study they showed the least immunogenicity as well, with OD 1 at ~22K. However, these titers show boosting effect, and therefore, it is likely that we can over come restriction by multiple immunizations.

Figure 6:
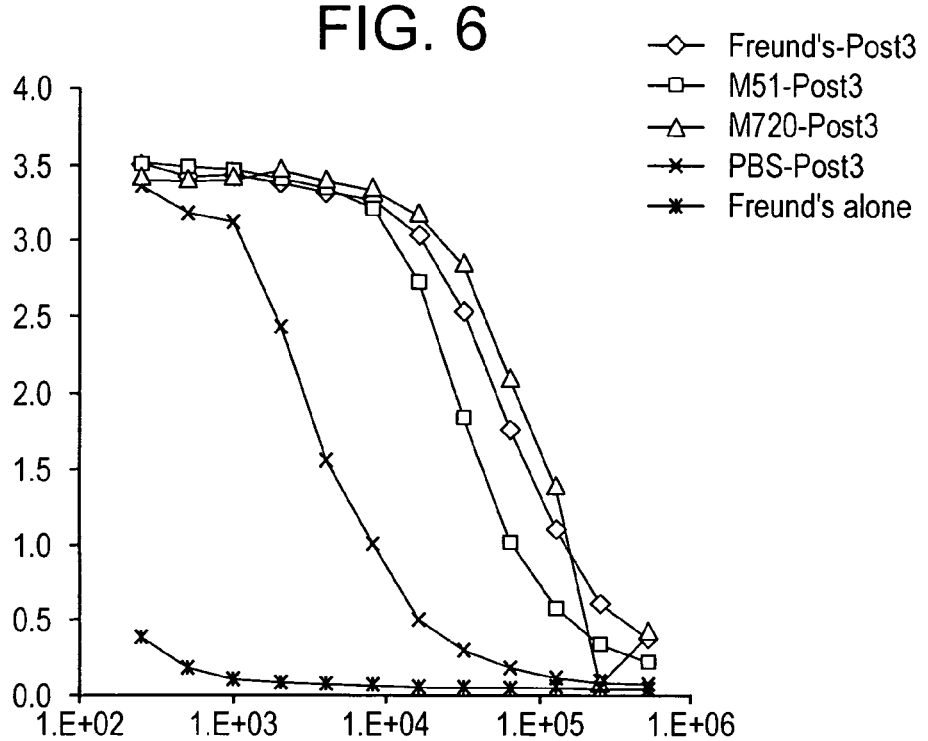
FIG. 6. Immunogenicity of CS: Effect of different adjuvants on immunogenicity of CS in C57Bl/6 mice.

While many antigens show good immune responses in animals using a strong adjuvant like Freund's, a true test would be to see if the protein is immunogenic using other adjuvants, such as Montanide, that are allowed for human use. We therefore, immunized C57Bl/6 mice with 1 μg protein emulsified with Freund's, Montanide 51, or Montanide 720. Mice were also immunized with protein in PBS alone. While mice immunized with protein emulsified with adjuvant started showing antibody responses following a single immunization with 1 μg protein (data not shown) following three immunizations two groups of mice, those immunized with Freund's and Montanide 720 reached titers of greater than 128K. Montanide 51 appears to be less immunogenic, with titers of 64K. Mice immunized with recombinant protein in. PBS also showed low titers. FIG. 6.

Thus, the antibody analysis shows that recombinant CS is highly immunogenic and the immune response transcends genetic restriction and is not dependent on adjuvant (or this response is not adjuvant-dependent).

Example 5

Fine Mapping/Epitope Analysis of Immune Response

Figure 7:
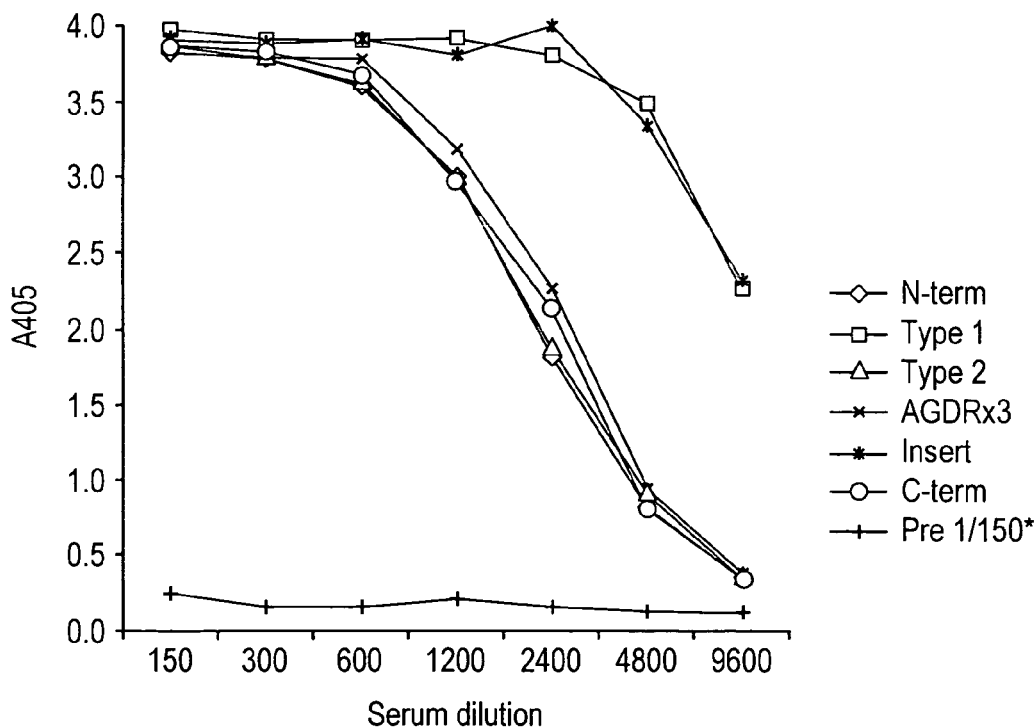
FIG. 7. Immunogenicity of CS: Epitope analysis of antibodies generated against CS.

In order to assess the fine specificity of the immune response we synthesized biotinylated peptides spanning the molecule. ELISA titers were detected to all the CS peptides. However, the titers varied. Type 1 peptide, which is represented in varying forms about nine times, had the highest titers of about 15,000 (FIG. 7). The 12 amino acid insert also had similar titers. The remaining peptides had lower titers ranging from about 4-5K. A scrambled peptide, and pre immune serum served as negative controls.

As discussed above, the exact role of various parts of CS molecule are not clearly known. Region I and II are known to be involved in Hepatocyte binding. The N-terminal part of CS has been shown to be important in binding to Heparan sulfate and hepatocytes. Truncation of the first 41 amino acids abrogates hepatocytes binding (Rathore et al. 2002, J. Biol. Chem. 277, 7092-8). The repeat region has also been implicated in protection. A monoclonal antibody that has been mapped to a four amino acid motif (AGDR) within the VK210 sequence protected monkeys that were immunized passively with this antibody (Charoenvit et al., 1991, Science 251, 668). In a study using synthetic MAPs as vaccines, there was a positive correlation between protection and anti-AGDR titers (Udhaykumar et al., 1998, Vaccine 16, 982-8).

Our results show that our recombinant protein is able to induce antibodies recognizing both VK210 and VK247 sequences. If anti-repeat antibodies play an important role in protection, then our construct generates antibodies that should be able to recognize, and neutralize, both types of sporozoites. Additionally, we are able to generate antibodies against the AGDR motif, which is a part of the central repeat region and has been shown to correlate to protection.

Representative peptides in the N- and C-terminal region were also recognized indicating that all parts of the molecules are being exposed and being recognized by the immune system. The fact that we were able to detect antibodies to Region I suggests that immunization with our construct may prevent the receptor/ligand interaction (which is an essential step in invasion).

Isolates with prolonged latent periods have been shown to have a 12 amino acid insert. While antibodies to the chimeric antigen recognize this insert the significance in establishing protective immune responses are not known.

Example 6

Reactivity of Anti-CS Antibodies to Native CS

Figure 8:
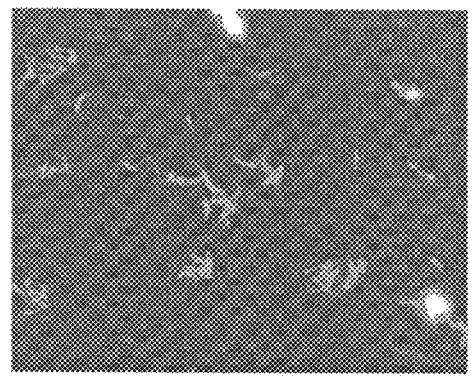
FIG. 8. Recognition of live sporozoites by antibodies generated against CS.

In order to test if antibodies generated against this chimeric molecule are able to recognize native protein we performed immunofluorescence assays with live Pv210 sporozoites that were freshly harvested from the salivary gland. Immune serum showed positive staining (FIG. 8) while the pre-immune serum was negative (data not shown). The sporozoites showed clumping in the presence of immune serum. Such clumping inactivates the sporozoites and renders them noninfectious (Vanderberg and Frevert 2004, Int. J. Parasitol. 34, 991-6). Elegant studies done by Vanderburg using intravital microscopy demonstrated that mice that were immunized with irradiated sporozoites and high titer antibodies to sporozoites prevented the sporozoites from migrating from the skin into blood vessels. Thus, clumping, and resulting inactivation of the sporozoites may prevent the onset of the hepatic stage of infection in individuals immunized with recombinant CS.

Figure 9A:
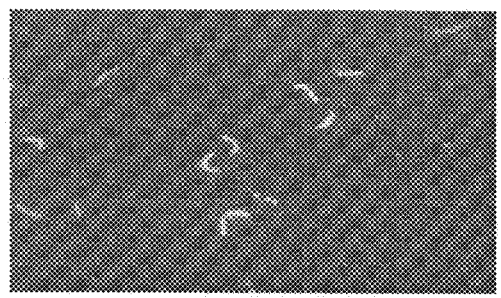
FIGS. 9A and 9B. Recognition of Type 1 (9A) and Type 2 (9B) sporozoites by antibodies generated against CS.
Figure 9B:
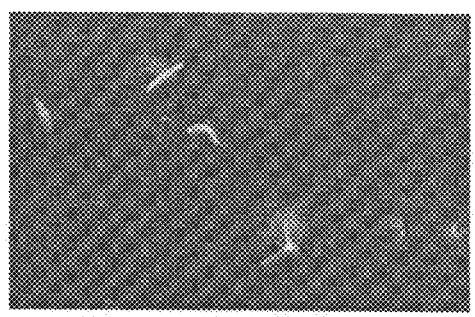

Based on the ELISA reactivity, it appears that immunization with the hybrid CS molecule generated antibodies against both VK210 and VK247 2 peptides. We confirmed this reactivity using both VK210 and VK247 sporozoites. Sera from immunized mice recognized both Type 1 and Type 2 sporozoites (FIGS. 9A and B).

Example 7

Induction of Cellular Responses in Mice

Interferon gamma production has been shown to correlate with protection during the pre-erythrocytic infection. In order to assess if immunization with recombinant CS activates the cellular response, we immunized C57Bl/6 mice with 10 ug protein, adjuvanted with Montanide 51, twice and harvested the spleens two weeks following the last immunization. The immunized mice showed the production of Interferon gamma which can also be used as a surrogate marker for the generation of a cellular response.

Thus, we report the design, construction, expression and purification of a recombinant chimeric CS protein that encodes for the extracellular portion of CS molecule and contains epitopes for both VK210, and VK247 repeat region. Our construct is highly immunogenic and is able to induce high-titered antibodies in both Outbred, and Inbred mice. These antibodies are not restricted to the normally immunodominant repeat region. We detect antibodies directed against various parts of the molecule. These antibodies recognize the native CS molecule on the surface of sporozoites and are capable of inactivating live sporozoites. Based on these characteristics we feel that our recombinant molecule is a strong candidate for a pre-erythrocytic vaccine for all strains and isolates of *P. vivax*.

What is claimed is:

1. A purified *P. vivax* circumsporozoite hybrid (PvCS-hybrid) protein comprising conserved Region I set forth as SEQ ID NO: 1, conserved Region II plus set forth as SEQ ID NO: 2, Type I repeats set forth as SEQ ID NO: 3-9, Type II repeats set forth as SEQ ID NO: 11 and SEQ ID NO: 14, and a 12 amino acid insert set forth as SEQ ID NO: 11.

2. The PvCS-hybrid of claim 1 wherein said Type I repeats number 9.

3. The PvCS-hybrid of claim 1 wherein said Type II repeats number 1.

4. The PvCS-hybrid of claim 1 wherein said Type I repeats number 9 and said Type II repeats number 1.

5. The PvCS-hybrid of claim 4 identified in SEQ ID NO:13.

6. An immunogenic composition comprising the protein of claim 5.

7. The composition of claim 6 further comprising an adjuvant.

8. A vaccine against *P. vivax* malaria comprising PvCS-hybrid according to claim 5.

9. The vaccine of claim 8 further comprising an adjuvant.

10. The vaccine of claim 9 wherein said adjuvant is montanide.

11. A kit for determining the presence of malaria antibodies in a biological sample, comprising:
   a composition comprising the protein of claim 5
   a buffer or components necessary for producing a buffer;
   means for detecting immune complexes formed between the protein and antibodies present in the sample.

12. A kit for monitoring malaria infection or prognosing the response to treatment of patients suffering from malaria infection comprising:
   a composition comprising the PvCS-hybrid protein of claim 5
   a buffer or buffer components
   means for detecting the immune complexes formed between the protein and antibodies present in the sample, and
   optionally, a means for determining the amount of immune complex formed.

13. A method for in vitro diagnosis of malaria antibodies in a biological sample, comprising
   (i) contacting said biological sample with a composition comprising the PvCS-hybrid protein of claim 5 under appropriate conditions which allow the formation of an immune complex, wherein said peptide is labeled with a detectable label, and
   (ii) detecting the presence of said immune complexes visually or mechanically.

14. A method for inducing in a subject an immune response against *P. vivax* comprising administering to said subject a composition comprising an immunologically effective amount of PvCS-hybrid of claim 5 in an acceptable diluent.

15. The method of claim 14 wherein said composition further comprises an adjuvant.

16. The method of claim 15 wherein said adjuvant is montanide.

17. A method for inducing a protective immune response to *P. vivax* malaria in a mammal, comprising
   administering a composition comprising a protein according to claim 5 in an amount effective to induce an immune response in said mammal.

18. The method according to claim 17 wherein the composition further comprises an adjuvant.

19. The method according to claim 18 wherein said adjuvant is montanide.

* * * * *

SEQUENCE LISTING

```
<160> NUMBER OF SEQ ID NOS: 14

<210> SEQ ID NO 1
<211> LENGTH: 5
<212> TYPE: PRT
<213> ORGANISM: Plasmodium vivax
<220> FEATURE:

<400> SEQUENCE: 1

Lys Leu Lys Gln Pro
                5

<210> SEQ ID NO 2
<211> LENGTH: 6
<212> TYPE: PRT
<213> ORGANISM: Plasmodium vivax
<220> FEATURE:

<400> SEQUENCE: 2

Cys Ser Val Thr Cys Gly
                5
```

```
<210> SEQ ID NO 3
<211> LENGTH: 9
<212> TYPE: PRT
<213> ORGANISM: Plasmodium vivax
<220> FEATURE:

<400> SEQUENCE: 3

Gly Asp Arg Ala Ala Gly Gln Pro Ala
                5

<210> SEQ ID NO 4
<211> LENGTH: 9
<212> TYPE: PRT
<213> ORGANISM: Plasmodium vivax
<220> FEATURE:

<400> SEQUENCE: 4

Gly Asp Arg Ala Asp Gly Gln Pro Ala
                5

<210> SEQ ID NO 5
<211> LENGTH: 9
<212> TYPE: PRT
<213> ORGANISM: Plasmodium vivax
<220> FEATURE:

<400> SEQUENCE: 5

Gly Asp Arg Ala Asp Gly Gln Ala Ala
                5

<210> SEQ ID NO 6
<211> LENGTH: 9
<212> TYPE: PRT
<213> ORGANISM: Plasmodium vivax
<220> FEATURE:

<400> SEQUENCE: 6

Gly Asn Gly Ala Gly Gly Gln Pro Ala
                5

<210> SEQ ID NO 7
<211> LENGTH: 9
<212> TYPE: PRT
<213> ORGANISM: Plasmodium vivax
<220> FEATURE:

<400> SEQUENCE: 7

Gly Asp Gly Ala Ala Gly Gln Pro Ala
                5

<210> SEQ ID NO 8
<211> LENGTH: 10
<212> TYPE: PRT
<213> ORGANISM: Plasmodium vivax
<220> FEATURE:

<400> SEQUENCE: 8

Gly Asp Arg Ala Ala Arg Gly Gln Ala Ala
                5                   10

<210> SEQ ID NO 9
<211> LENGTH: 9
<212> TYPE: PRT
<213> ORGANISM: Plasmodium vivax
<220> FEATURE:

<400> SEQUENCE: 9
```

-continued

Gly Asn Gly Ala Gly Gly Gln Ala Ala
                5

<210> SEQ ID NO 10
<211> LENGTH: 9
<212> TYPE: PRT
<213> ORGANISM: Plasmodium vivax
<220> FEATURE:

<400> SEQUENCE: 10

Ala Asn Gly Ala Gly Asn Gln Pro Gly
                5

<210> SEQ ID NO 11
<211> LENGTH: 12
<212> TYPE: PRT
<213> ORGANISM: Plasmodium vivax
<220> FEATURE:

<400> SEQUENCE: 11

Gly Gly Asn Ala Ala Asn Lys Lys Ala Glu
                5                   10

Asp Ala

<210> SEQ ID NO 12
<211> LENGTH: 771
<212> TYPE: DNA
<213> ORGANISM: Plasmodium vivax
<220> FEATURE:

<400> SEQUENCE: 12

| | | |
|---|---|---|
| acacattgcg gacataatgt agatttatct aaagctataa | 40 |
| atttaaatgg tgtaaacttc aataacgtag acgctagttc | 80 |
| actcggggct gcgcacgtag gtcagtctgc tagcaggggg | 120 |
| cgcggtctcg gggaaaaccc agacgacgaa gaaggtgatg | 160 |
| ctaaaaagaa aaaggacggt aaaaaagcgg aaccaaaaaa | 200 |
| tccagggaa aataaattaa aacagcccgg ggatcgcgcg | 240 |
| gatggtcaag cggcgggtaa tggggcgggg ggtcaaccag | 280 |
| cgggggatcg cgcggctggt cagccagcgg gggatcgcgc | 320 |
| ggctggtcag ccagcggggg atggtgcggc tggccaacca | 360 |
| gcggggatc gcgcggatgg tcagccagcg ggggatcgcg | 400 |
| cggatggtca accagccggt gatcgcgcgg ctggccaagc | 440 |
| ggccggtaat ggggcggggg gtcaagcggc gcgaacgga | 480 |
| gcggggaacc agccaggcgg cggtaacgct gcgaataaaa | 520 |
| aagcggaaga tgcgggtggt aacgcgggcg gtaatgcggg | 560 |
| cggccaaggt cagaacaacg aagggctaa tgcaccaaac | 600 |
| gaaaaatctg tcaagaata tctcgataaa gtccgcgcta | 640 |
| cagtagggac agaatggacg ccatgctctg taacatgtgg | 680 |
| tgtcggggta cgcgtgcgcc gccgtgtcaa tgcggctaac | 720 |
| aaaaaaccag aagatctcac gttaaatgat ctcgaaacgg | 760 |
| atgtctgcac a | 771 |

```
<210> SEQ ID NO 13
<211> LENGTH: 257
<212> TYPE: PRT
<213> ORGANISM: Plasmodium vivax
<220> FEATURE:

<400> SEQUENCE: 13

Thr His Cys Gly His Asn Val Asp Leu Ser
                  5                  10

Lys Ala Ile Asn Leu Asn Gly Val Asn Phe
                 15                  20

Asn Asn Val Asp Ala Ser Ser Leu Gly Ala
                 25                  30

Ala His Val Gly Gln Ser Ala Ser Arg Gly
                 35                  40

Arg Gly Leu Gly Glu Asn Pro Asp Asp Glu
                 45                  50

Glu Gly Asp Ala Lys Lys Lys Asp Gly
                 55                  60

Lys Lys Ala Glu Pro Lys Asn Pro Arg Glu
                 65                  70

Asn Lys Leu Lys Gln Pro Gly Asp Arg Ala
                 75                  80

Asp Gly Gln Ala Ala Gly Asn Gly Ala Gly
                 85                  90

Gly Gln Pro Ala Gly Asp Arg Ala Ala Gly
                 95                 100

Gln Pro Ala Gly Asp Arg Ala Ala Gly Gln
                105                 110

Pro Ala Gly Asp Gly Ala Ala Gly Gln Pro
                115                 120

Ala Gly Asp Arg Ala Asp Gly Gln Pro Ala
                125                 130

Gly Asp Arg Ala Asp Gly Gln Pro Ala Gly
                135                 140

Asp Arg Ala Ala Gly Gln Ala Ala Gly Asn
                145                 150

Gly Ala Gly Gly Gln Ala Ala Ala Asn Gly
                155                 160

Ala Gly Asn Gln Pro Gly Gly Gly Asn Ala
                165                 170

Ala Asn Lys Lys Ala Glu Asp Ala Gly Gly
                175                 180

Asn Ala Gly Gly Asn Ala Gly Gly Gln Gly
                185                 190

Gln Asn Asn Glu Gly Ala Asn Ala Pro Asn
                195                 200

Glu Lys Ser Val Lys Glu Tyr Leu Asp Lys
                205                 210

Val Arg Ala Thr Val Gly Thr Glu Trp Thr
                215                 220

Pro Cys Ser Val Thr Cys Gly Val Gly Val
                225                 230

Arg Val Arg Arg Arg Val Asn Ala Ala Asn
```

```
                      235                 240
Lys Lys Pro Glu Asp Leu Thr Leu Asn Asp
                      245                 250
Leu Glu Thr Asp Val Cys Thr
                      255

<210> SEQ ID NO 14
<211> LENGTH: 9
<212> TYPE: PRT
<213> ORGANISM: Plasmodium vivax
<220> FEATURE:

<400> SEQUENCE: 14

Ala Asn Gly Ala Gly Asp Gln Pro Gly
                     5
```